(12) United States Patent
Sekido

(10) Patent No.: US 10,966,594 B2
(45) Date of Patent: Apr. 6, 2021

(54) IMAGING DEVICE, ENDOSCOPE, AND METHOD OF MANUFACTURING IMAGING DEVICE

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 328 days.

(21) Appl. No.: 16/032,122

(22) Filed: Jul. 11, 2018

(65) Prior Publication Data

US 2018/0325360 A1    Nov. 15, 2018

Related U.S. Application Data

(63) Continuation of application No. PCT/JP2016/051045, filed on Jan. 14, 2016.

(51) Int. Cl.
*A61B 1/00* (2006.01)
*H01L 27/14* (2006.01)
(Continued)

(52) U.S. Cl.
CPC ........ *A61B 1/00124* (2013.01); *A61B 1/0011* (2013.01); *A61B 1/00096* (2013.01);
(Continued)

(58) Field of Classification Search
CPC ............ A61B 1/00124; A61B 1/00096; A61B 1/0011; A61B 1/00114; A61B 1/00188; A61B 1/051

See application file for complete search history.

(56) References Cited

U.S. PATENT DOCUMENTS 4,745,470 A * 5/1988 Yabe .................... H04N 5/2253
   348/76
4,831,456 A * 5/1989 Takamura ................ A61B 1/05
   348/294
(Continued)

FOREIGN PATENT DOCUMENTS

JP        03162839 A  *  7/1991
JP     H09-061731 A      3/1997
(Continued)

OTHER PUBLICATIONS

International Search Report dated Apr. 19, 2016 issued in PCT/JP2016/051045.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An imaging device that includes at least one lens that collects light incident from an object; an imaging sensor that receives light from the lens and converts it to an electric signal; a multi-layer substrate electrically connected to the imaging sensor that includes electronic components and conductive layers and vias; and a collective cable including at least one coaxial cable. A core connection electrode connected to a core of the coaxial cable is formed on a first surface of the multi-layer substrate, the first substrate intersecting with a height direction of the multi-layer substrate. A shielded-wire connection electrode connected to a shielded wire of the coaxial cable is formed on a side surface of the multi-layer substrate adjacent to the first surface. The side surface faces and the cable extend to a proximal end.

7 Claims, 6 Drawing Sheets

(51) Int. Cl.
  *B23K 1/005* (2006.01)
  *H04N 7/18* (2006.01)
  *G02B 23/24* (2006.01)
  *A61B 1/05* (2006.01)
  *B23K 1/00* (2006.01)
  B23K 101/38 (2006.01)
  H04N 5/225 (2006.01)
  H01L 27/146 (2006.01)
  H01R 24/50 (2011.01)
  H01R 103/00 (2006.01)

(52) U.S. Cl.
  CPC ...... *A61B 1/00114* (2013.01); *A61B 1/00188* (2013.01); *A61B 1/00195* (2013.01); *A61B 1/05* (2013.01); *A61B 1/051* (2013.01); *B23K 1/0008* (2013.01); *B23K 1/0056* (2013.01); *G02B 23/24* (2013.01); *H01L 27/14* (2013.01); *H04N 7/18* (2013.01); B23K 2101/38 (2018.08); H01L 27/14627 (2013.01); H01R 24/50 (2013.01); H01R 2103/00 (2013.01); H04N 2005/2255 (2013.01)

(56) References Cited

U.S. PATENT DOCUMENTS

| | | | | |
|---|---|---|---|---|
| 4,832,003 A | * | 5/1989 | Yabe | A61B 1/051 |
| | | | | 348/65 |
| 9,774,151 B2 | * | 9/2017 | Kobayashi | H01R 24/38 |
| 10,312,566 B2 | * | 6/2019 | Yamada | H01P 5/08 |
| 2009/0185032 A1 | * | 7/2009 | Sakai | A61B 1/00096 |
| | | | | 348/65 |
| 2009/0303619 A1 | * | 12/2009 | Iwasaki | G02B 23/243 |
| | | | | 359/811 |
| 2012/0104230 A1 | * | 5/2012 | Eismann | H04N 5/2253 |
| | | | | 250/208.1 |
| 2013/0005181 A1 | * | 1/2013 | Yamada | H01R 9/0515 |
| | | | | 439/578 |
| 2014/0326857 A1 | * | 11/2014 | Sekido | H01L 27/14636 |
| | | | | 250/208.1 |
| 2015/0190039 A1 | * | 7/2015 | Takahashi | A61B 1/00009 |
| | | | | 600/109 |
| 2015/0358519 A1 | * | 12/2015 | Kamei | H04N 5/2254 |
| | | | | 348/68 |
| 2016/0005513 A1 | * | 1/2016 | Sekido | H01B 7/0216 |
| | | | | 174/74 R |
| 2016/0209637 A1 | * | 7/2016 | Fujimori | H04N 5/374 |
| 2017/0035279 A1 | * | 2/2017 | Fujii | A61B 1/051 |
| 2017/0301433 A1 | * | 10/2017 | Sekido | H01R 43/0256 |
| 2018/0249896 A1 | * | 9/2018 | Mikami | H01R 4/027 |
| 2019/0069767 A1 | * | 3/2019 | Mikami | A61B 1/005 |
| 2019/0343375 A1 | * | 11/2019 | Sato | A61B 1/051 |
| 2019/0350555 A1 | * | 11/2019 | Wakabayashi | A61B 8/4488 |
| 2020/0084343 A1 | * | 3/2020 | Sekido | H01R 13/5221 |
| 2020/0163535 A1 | * | 5/2020 | Sekido | H01L 24/92 |

FOREIGN PATENT DOCUMENTS

| | | | |
|---|---|---|---|
| JP | 2003-010111 A | | 1/2003 |
| JP | 2005-193059 A | | 7/2005 |
| JP | 2011071036 A | * | 4/2011 |
| JP | 2018137234 A | * | 8/2018 |

* cited by examiner

IMAGING DEVICE, ENDOSCOPE, AND METHOD OF MANUFACTURING IMAGING DEVICE

CROSS-REFERENCE TO RELATED APPLICATION

This application is a continuation of International Application No. PCT/JP2016/051045, filed on Jan. 14, 2016, the entire contents of which are incorporated herein by reference.

BACKGROUND OF THE INVENTION

1. Field of the Invention

The present disclosure relates to an imaging device, an endoscope, and a method of manufacturing the imaging device.

2. Description of the Related Art

In the past, endoscopes have been widely used for various types of examination in medical fields and industrial fields. Among them, medical endoscopes may acquire in-vivo images within a body cavity without making an incision in a subject such as patient by inserting an elongated flexible insertion unit with an imaging element provided at its distal end into the body cavity of the subject. Furthermore, endoscopes are widely used because they are capable of making treatment by protruding a treatment tool from the distal end of the insertion unit if needed.

At the distal end of the insertion unit of this type of endoscope, an imaging device is installed which includes a solid state image sensor and a multi-layer substrate on which electronic components such as capacitors and IC chips that constitute a drive circuit of the solid state image sensor and signal cables are installed. With regard to a signal cable connected to the multi-layer substrate at the proximal end side, it is necessary that the overall cover of a collective cable is removed and a signal cable to be connected is drawn and located at a connection position by using a jig, or the like. Because the part needed for drawing signal cables from the collective cable is a hard part of the endoscope, various considerations are given to downsize the hard part so as to decrease loads on the subject.

As a technology for shortening a length of a hard part at the distal end of an endoscope with a built-in imaging unit, there is a disclosure of the technology of an imaging unit where electronic components and signal cables are connected to the inner circumference of a circuit board that is formed like a polygonal shape, a signal cable is connected at the side closer to the solid state image sensor than electronic components, and the electronic components are installed in the part necessary for drawing the signal cable (for example, see Japanese Laid-open Patent Publication No. 09-61731).

SUMMARY OF THE INVENTION

According to a first aspect of the present disclosure, there is provided an imaging device including at least one objective lens collecting light incident from an object to be imaged; an imaging sensor receiving light from the at least one objective lens and converting the received light to an electric signal; a multi-layer substrate electrically connected to the imaging sensor, the multi-layer substrate including electronic components installed thereon and electrically conductive layers and vias that are formed therein; and a collective cable including at least one coaxial cable connected to the multi-layer substrate. In the imaging device, a core connection electrode to which a core of the coaxial cable is connected is formed on a first surface of the multi-layer substrate, the first substrate intersecting with a height direction of the multi-layer substrate, and a shielded-wire connection electrode to which a shielded wire of the coaxial cable is connected is formed on a second surface of the multi-layer substrate that is adjacent to the first surface of the multi-layer substrate and that faces to a proximal end from which the collective cable extends.

According to a second aspect of the present disclosure, there is provided an endoscope including the imaging device according to the first aspect; and an insertion unit that includes a distal end part made of hard material in cylindrical shape and that may be inserted into a subject.

According to a third aspect of the present disclosure, there is provided a method for manufacturing an imaging device. The method includes connecting the shielded wire of the coaxial cable to the shielded-wire connection electrode of the multi-layer substrate, the core of the coaxial cable, an internal insulating member that covers an outer circumference of the core, and the shielded wire that covers an outer circumference of the internal insulating member being gradually exposed from an external insulating member that covers an outer circumference of the shielded wire; and connecting the core to the core connection electrode. The connecting of the shielded wire includes heating the shielded wire by using a heater chip from the height direction of the multi-layer substrate and applying heat by emitting laser light or soft beam to the conductive land formed in a direction of the third surface of the shielded-wire connection electrode from a direction of the third surface of the multi-layer substrate to melt solder so as to connect the shielded wire to the shielded-wire connection electrode.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Figure 1:
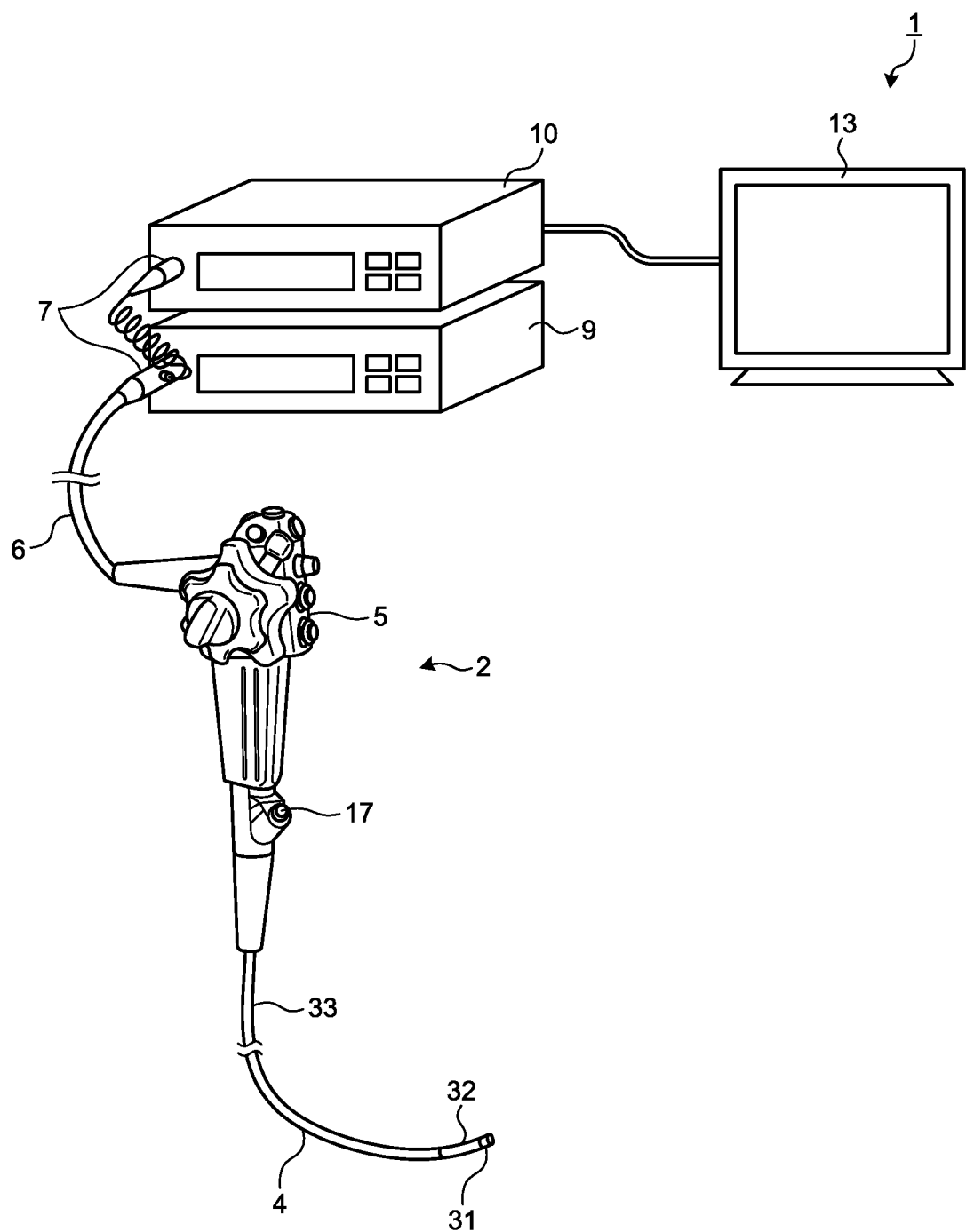
FIG. 1 is a diagram that schematically illustrates the overall configuration of an endoscope system according to a first embodiment of the present disclosure.

An explanation is given below of an endoscope including an imaging device as an aspect (hereafter, referred to as "embodiment") for implementing the present disclosure. Furthermore, the embodiment is not a limitation on the present disclosure. Moreover, in description of drawings, the same components are attached with the same reference numeral. Moreover, it should be noted that the drawings are schematic and the relation between members in thickness and width, the ratio between members, and the like, are differ from reality. Moreover, each of the drawings contains parts that are different in dimension or proportion.

First Embodiment

FIG. 1 is a diagram that schematically illustrates the overall configuration of an endoscope system according to a first embodiment of the present disclosure. As illustrated in FIG. 1, an endoscope system 1 includes an endoscope 2, a universal cord 6, a connector 7, a light source device 9, a processor (control device) 10, and a display device 13.

The endoscope 2 has an insertion unit 4 inserted into the body cavity of a subject so as to capture in-vivo images of the subject and output imaging signals. A bundle of electric cables inside the universal cord 6 extends up to the distal end of the insertion unit 4 in the endoscope 2 and connects to the imaging device provided in a distal end part 31 of the insertion unit 4.

The connector 7 is provided at the proximal end of the universal cord 6 and is connected to the light source device 9 and the processor 10 where predetermined signal processing is performed on imaging signals output from the imaging device in the distal end part 31 connected to the universal cord 6 and where analog-digital conversion (A/D conversion) is conducted on imaging signals thereby to be output as image signals.

The light source device 9 includes, for example, a white light emitting diode (LED). Pulsed white light emitted from the light source device 9 passes through the connector 7 and the universal cord 6 and is emitted from the distal end of the insertion unit 4 in the endoscope 2 toward an object, as illumination light.

The processor 10 conducts predetermined image processing on image signals output from the connector 7 and performs overall control of the endoscope system 1. The display device 13 displays image signals processed by the processor 10.

The proximal end side of the insertion unit 4 in the endoscope 2 is connected to an operating unit 5 that is provided with various types of buttons or knobs to perform endoscope functions. The operating unit 5 is provided with a treatment-tool insertion opening 17 through which a treatment tool, such as biopsy forceps, electric cautery, or examination probe, is inserted into the body cavity of a subject.

The insertion unit 4 includes the distal end part 31 in which the imaging device is provided; a curved portion 32 that is continuous with the proximal end side of the distal end part 31 and is flexibly curved in multiple directions; and a flexible tube portion 33 that is continuous with the proximal end side of the curved portion 32. The curved portion 32 is curved due to operation of a curving-operation knob provided in the operating unit 5 and, in accordance with pulling and loosening of a curving-operation wire inserted inside the insertion unit 4, is flexibly curved in four directions, e.g., upward, downward, leftward, and rightward.

The endoscope 2 is provided with a light guide bundle (not illustrated) for guiding the illumination light from the light source device 9, and an illumination lens (not illustrated) is provided at an illumination light output end of the light guide bundle. Specifically, the illumination lens is provided in the distal end part 31 of the insertion unit 4, and the illumination light is emitted through the illumination lens toward the subject.

Figure 2:
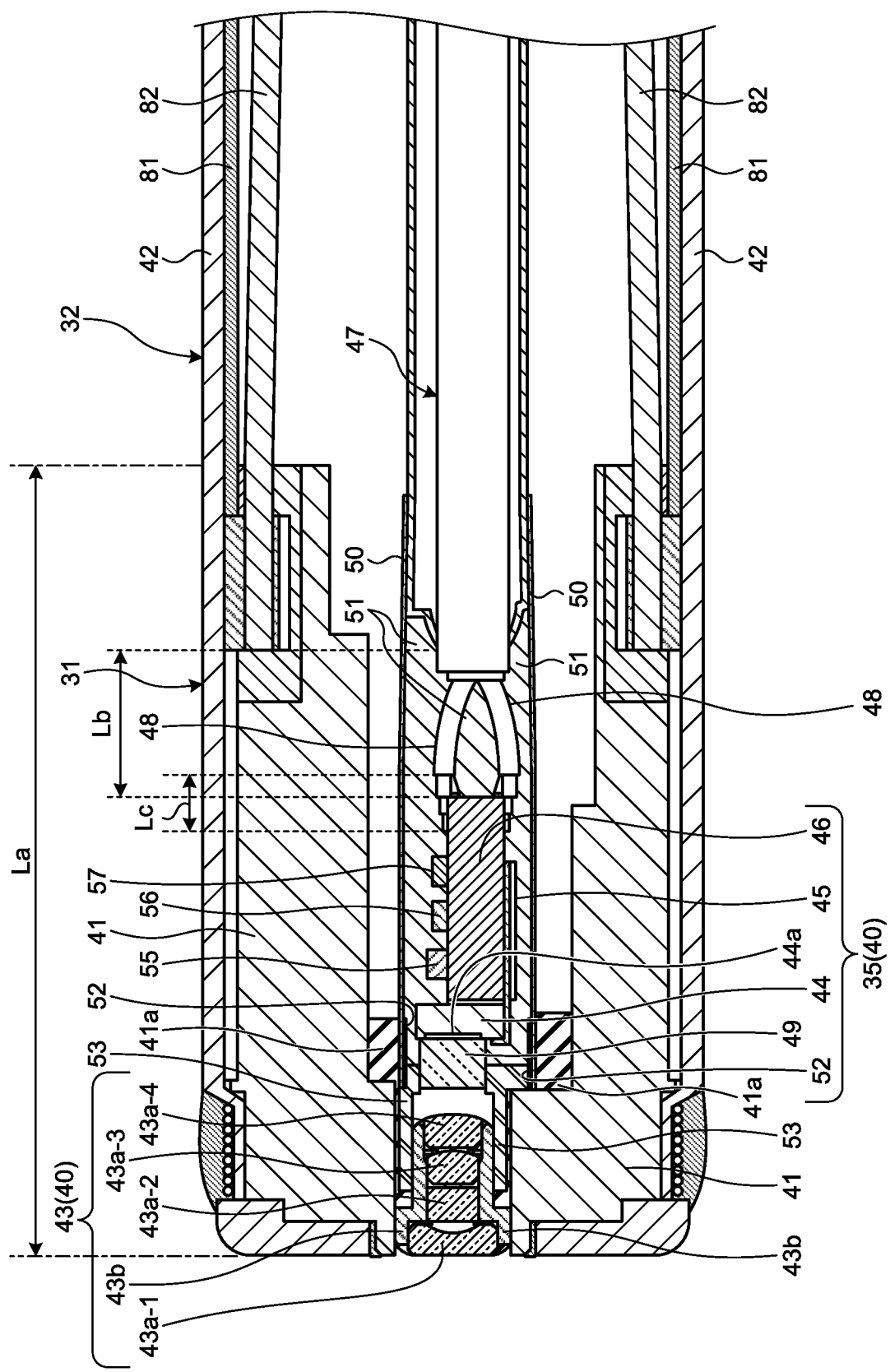
FIG. 2 is a partial cross-sectional view of the distal end of an endoscope illustrated in FIG. 1.
Figure 3:
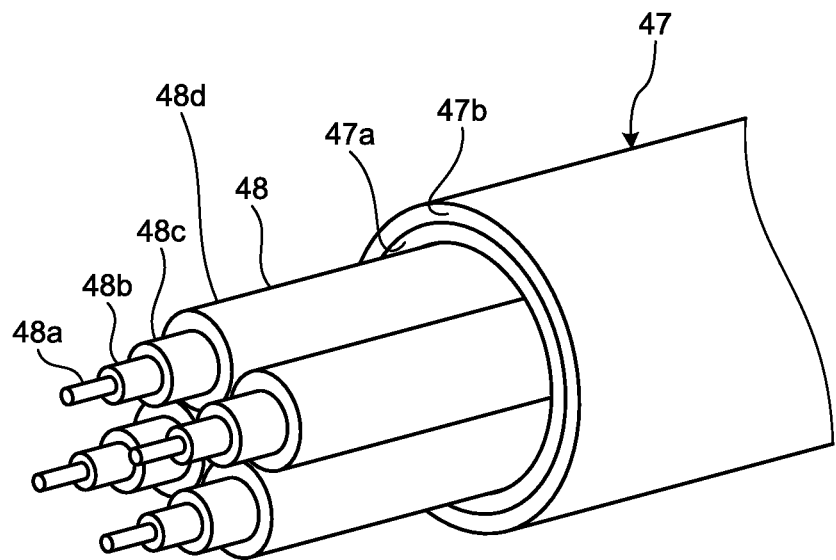
FIG. 3 is a perspective view of a collective cable used in the first embodiment of the present disclosure.

Next, a configuration of the distal end part 31 of the endoscope 2 is explained in detail. FIG. 2 is a partial cross-sectional view of the distal end of the endoscope 2. FIG. 3 is a perspective view of a collective cable used in the first embodiment of the present disclosure. Here, FIG. 2 is a cross-sectional view that is cross-section on the plane that is perpendicular to the substrate surface of an imaging device 40 provided in the distal end part 31 of the endoscope 2 and that is parallel to the optical axis direction of an imaging unit. The distal end part 31 of the insertion unit 4 in the endoscope 2 and part of the curved portion 32 are illustrated in FIG. 2.

As illustrated in FIG. 2, the curved portion 32 is flexibly curved in four directions, upward, downward, leftward, and rightward, in accordance with pulling and loosening of a curving-operation wire 82 that is inserted inside a curved tube 81 provided on the inner side of a cover tube 42 described later. The imaging device 40 is provided inside the distal end part 31 that extends from the distal end side of the curved portion 32.

The imaging device 40 includes a lens unit 43 and an imaging unit 35 provided on the proximal end side of the lens unit 43. The imaging device 40 is glued to the inner side of a distal-end main body 41 with an adhesive agent 41a. The distal-end main body 41 is made of hard material for forming an inner space in which the imaging device 40 is to be accommodated. The proximal-end outer circumference of the distal-end main body 41 is covered with the soft cover tube 42. A member on the proximal end side of the distal-end main body 41 is made of soft material so that the curved portion 32 may be curved. The distal end part 31 in which the distal-end main body 41 is provided is a hard part of the insertion unit 4. A length La of the hard part is from the distal end of the insertion unit 4 to the proximal end of the distal-end main body 41.

The lens unit 43 includes objective lenses 43a-1 43a-2, 43a-3, and 43a-4 and a lens holder 43b that holds the objective lenses 43a-1 to 43a-4. The distal end of the lens holder 43b is inserted into and fitted in the inner side of the distal-end main body 41 so as to be fixed to the distal-end main body 41.

The imaging unit 35 includes a solid state image sensor 44, such as a Charge-Coupled Device (CCD) or Complementary Metal-Oxide-Semiconductor (CMOS), that receives light and conducts photoelectric conversion to generate electric signals; a flexible printed circuit substrate 45 (hereafter, referred to as "FPC substrate 45") extending on the back surface side opposed to the light receiving surface of a light receiving section 44a of the solid state image sensor 44; a multi-layer substrate 46 including conductor layers connected to a surface of the FPC substrate 45; and a glass lid 49 attached to the solid state image sensor 44 so as to cover the light receiving surface of the solid state image sensor 44. In the multi-layer substrate 46 of the imaging unit 35, electronic components 55, 56, and 57 that are active components included in a drive circuit of the solid state image sensor 44 are installed, and vias for electrically connecting unillustrated conductor layers are formed inside.

Referring to FIG. 3, a collective cable 47 includes four signal cables 48, each of which is a coaxial cable. The signal cables 48 are covered with an overall shield 47a, and the overall shield 47a is covered with an overall cover 47b. The overall shield 47a and the overall cover 47b are removed to predetermined lengths from the distal end part of the collective cable 47. Furthermore, each of the signal cables 48 includes a core 48a; an internal insulating member 48b that is provided on the outer circumference of the core 48a; a shielded wire 48c that covers the outer circumference of the internal insulating member 48b; and an external insulating member 48d that is provided on the outer circumference of the shielded wire 48c. The external insulating member 48d, and the like, are removed to predetermined lengths from the distal end part of the signal cable 48 such that the core 48a, the internal insulating member 48b, and the shielded wire 48c are exposed in a step-wise manner on the distal end part. According to the first embodiment, two of the signal cables 48 are connected to the respective surfaces, with which a height direction intersects, (i.e., the top surface and the bottom surface) of the multi-layer substrate 46.

Object images formed by the objective lenses 43a-1 to 43a-4 of the lens unit 43 are detected by the solid state image sensor 44 provided at the focus position of the objective lenses 43a-1 to 43a-4 and are converted into imaging signals. Imaging signals are output to the processor 10 through the signal cable 48 connected to the FPC substrate 45 and the multi-layer substrate 46 and the connector 7.

The solid state image sensor 44 is attached to the side surface of the multi-layer substrate 46 at the back surface side opposed to the light receiving surface where the light receiving section 44a is formed. The outer periphery of the side surface of the solid state image sensor 44 is covered with a metallic reinforcement member 52. To reduce influence of external static electricity on the electronic components 55, 56, 57 on the multi-layer substrate 46, the reinforcement member 52 is located away from the solid state image sensor 44, the FPC substrate 45, and the multi-layer substrate 46.

The imaging unit 35 and the distal end part of the collective cable 47 are surrounded by adhesive resin 51 which is in turn covered with a heat shrinkable tube 50 to improve durability.

The glass lid 49 is engaged into an inner space of a solid-state image sensor holder 53. With this, the solid-state image sensor holder 53 holds the glass lid 49 and thus the solid-stage image sensor 44 adhered onto the glass lid 49. The outer circumference of the solid-state image sensor holder 53 on the proximal end side is engaged with the inner circumference of the reinforcement member 52 on the distal end side. The outer circumference of the lens holder 43b on the proximal end side is engaged with the inner circumference of the solid-state image sensor holder 53 on the distal end side. In a state where the components are engaged with each other as described above, the outer circumference of the lens holder 43b, the outer circumference of the solid-state image sensor holder 53, and the outer circumference of the heat shrinkable tube 50 on the distal end side are secured to the inner circumference of the distal end of the distal-end main body 41 with the adhesive agent 41a.

Figure 4:
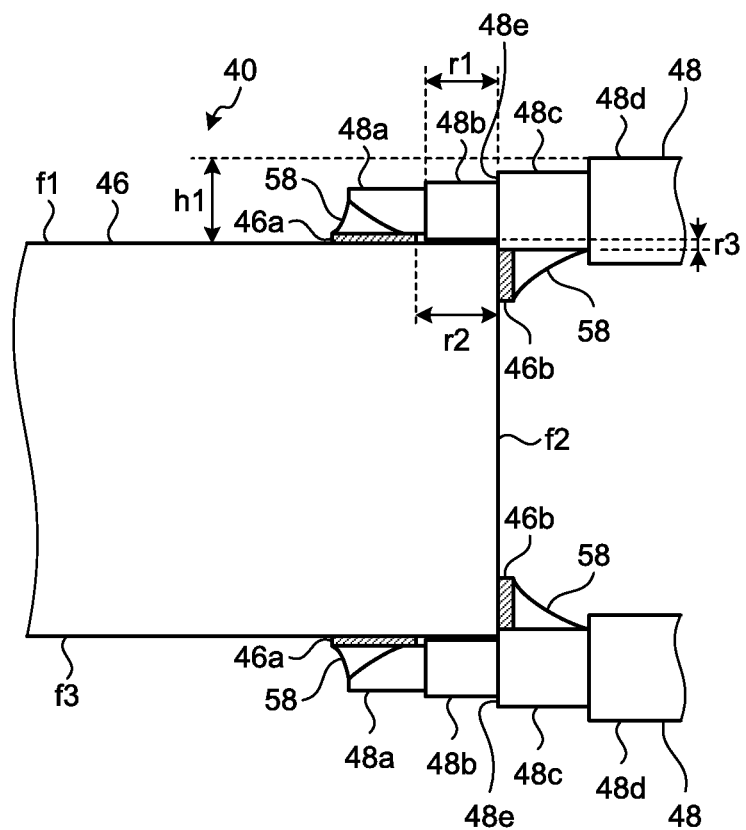
FIG. 4 is a partial side view of the proximal end part of a multi-layer substrate to which a signal cable is connected.

Next, with reference to FIG. 4, an explanation is given of the connection between the signal cable 48 and the multi-layer substrate 46. FIG. 4 is a partial side view of the proximal end part of the multi-layer substrate 46 to which the signal cable 48 is connected.

Core connection electrodes 46a for connecting the core 48a of the signal cable 48 are formed on the surfaces intersecting with the height direction of the multi-layer substrate 46, i.e., a top surface f1 and a bottom surface f3 of the rectangular multi-layer substrate 46. Shielded-wire connection electrodes 46b for connecting the shielded wire 48c are formed on the surface that is adjacent to the surfaces intersecting with the height direction of the multi-layer substrate 46, i.e., a side surface f2 facing to the proximal end from which the collective cable 47 extends. The core 48a and the shielded wire 48c are electrically and mechanically connected to the core connection electrode 46a and the shielded-wire connection electrode 46b, respectively, with solder 58.

The external insulating member 48d, and the like, are removed from the signal cable 48 such that, while the core 48a is located on the core connection electrode 46a, an end 48e of the shielded wire 48c is located on the side surface f2 of the multi-layer substrate 46 facing to the proximal end. The end 48e of the shielded wire 48c is located on the side surface f2 of the multi-layer substrate 46 facing to the proximal end. Namely, a length r1 of the exposed internal insulating member 48b is substantially identical to a length r2 from the end of the core connection electrode 46a to the side surface f2 facing to the proximal end so that the end 48e of the shielded wire 48c may abut the side surface f2 facing to the proximal end, thereby to be positioned therein. Furthermore, when the end 48e of the shielded wire 48c abuts the side surface f2 facing to the proximal end, thereby to be positioned therein, the shielded wire 48c is preferably reinforced by solder precoating, or the like.

The shielded-wire connection electrodes 46b are formed on the side surface f2 of the multi-layer substrate 46 facing to the proximal end and near the top surface f1 and the bottom surface f3 of the multi-layer substrate 46. It is preferable that ends of the shielded-wire connection electrodes 46b, the ends being closer to corresponding ones of the top surface f1 and the bottom surface f3 of the multi-layer substrate 46, are located at respective positions away from the top surface f1 and the bottom surface f3 along the height direction by equal to or less than a thickness r3 of the shielded wire 48c. Because the ends of the shielded-wire connection electrodes 46b are located at respective positions from the top surface f1 and the bottom surface f3 along the height direction by equal to or less than the thickness r3 of the shielded wire 48c, the side surface of the shielded wire 48c may abut the side surface of the shielded-wire connection electrode 46b, whereby the connection strength may be improved.

With regard to the collective cable 47 including the multiple (four) signal cables 48, to ensure that the core 48a and the shielded wire 48c of each of the signal cables 48 are connected to the multi-layer substrate 46, the signal cable 48 with the overall shield 47a and the overall cover 47b removed need to be drawn and located at a connection position by using a jig, or the like. A length Lb (see FIG. 2) of the part required to draw the signal cable 48 is generally determined by the type (materials of a conductor and an insulating member), the number, the outer diameter, and the like, of the signal cables 48 used. Furthermore, if the length Lb of the part required to draw the signal cable 48 is decreased, the length La of the distal-end main body 41 may be decreased; as a result, the length of a hard part may be shortened.

Furthermore, with regard to the connection of the core 48a and the shielded wire 48c to the multi-layer substrate 46, in order to ensure more than certain connection intensity, a length Lc required to connect the core 48a and the shielded wire 48c in an optical axis direction needs to be a predetermined length. If the core connection electrode 46a and the shielded-wire connection electrode 46b are provided on the top surface f1 and the bottom surface f3 of the multi-layer substrate 46, respectively, and the core 48a and the shielded wire 48c are connected to the core connection electrode 46a and the shielded-wire connection electrode 46b, respectively, the length Lc, in the optical axis direction, which is required to connect the core 48a and the shielded wire 48c to the multi-layer substrate 46, tends to be relatively longer.

Conversely, according to the first embodiment, because the shielded-wire connection electrode 46b is formed on the surface adjacent to the surface of the multi-layer substrate 46 along the height direction, i.e., the side surface f2 facing to the proximal end from which the collective cable 47 extends, part of the length Lc in an optical axis direction to connect the core 48a and the shielded wire 48c may be included in the length Lb required to draw the signal cable 48, and therefore the length La of the hard part may be shortened. Furthermore, because the shielded wire 48c is connected to the shielded-wire connection electrode 46b formed on the side surface f2 of the multi-layer substrate 46, a height h1 (FIG. 4) for connecting the signal cable 48 may be decreased, and the core 48a may be connected to the core connection electrode 46a without being folded. Thus, the reliability for connection of the core 48a may be improved.

Although in the above-described first embodiment an explanation is given of a case where the collective cable 47 including the four signal cables 48 is connected to the top surface f1 and the bottom surface f3 of the multi-layer substrate 46 by way of example only, the same advantage may be produced in a case where a collective cable includes two or more cables including at least one coaxial cable. Even in this case, the core connection electrode 46a is formed on only any surface of the multi-layer substrate 46, e.g., the top surface f1 or the bottom surface f3, with which the height direction of the multi-layer substrate 46 intersects, and the shielded-wire connection electrode 46b is formed on the surface that is adjacent to the surface where the core connection electrode 46a is formed and that faces to the proximal end.

Figure 5:
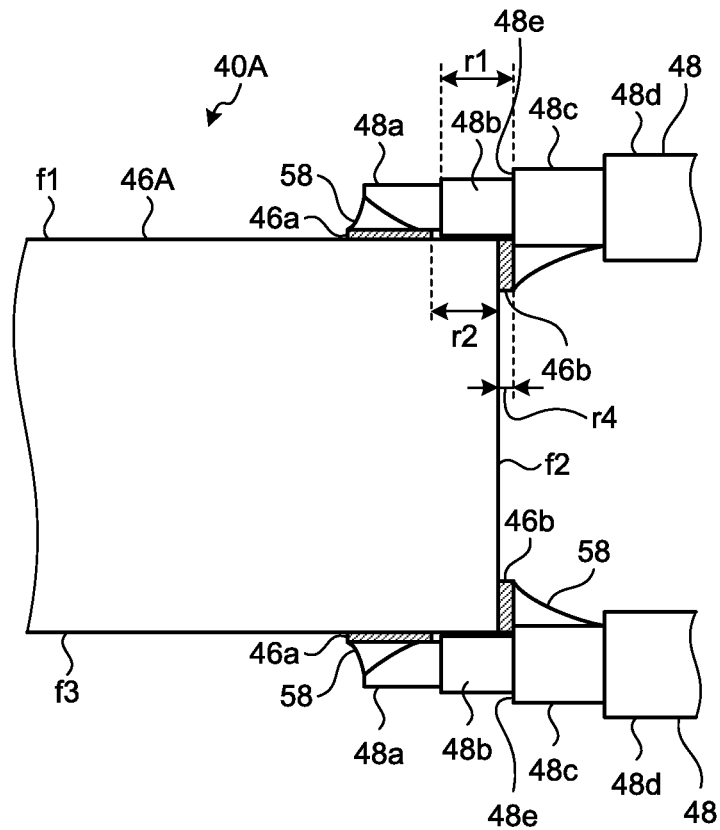
FIG. 5 is a partial side view of the proximal end part of a multi-layer substrate to which the signal cable is connected according to a modification 1 of the first embodiment of the present disclosure.

Furthermore, although in the above-described first embodiment, the shielded-wire connection electrodes 46b are provided such that they are located on the side surface f2 of the multi-layer substrate 46 facing to the proximal end and near the top surface f1 and the bottom surface f3 of the multi-layer substrate 46 along the height direction, they may be provided such that the end of the shielded-wire connection electrode 46b is located at the boundary between the side surface f2 facing to the proximal end and the top surface f1 or the bottom surface f3 of the multi-layer substrate 46 along the height direction. FIG. 5 is a partial side view of the proximal end part of a multi-layer substrate 46A to which the signal cable 48 is connected according to a modification 1 of the first embodiment of the present disclosure.

In an imaging device 40A, an end of the shielded-wire connection electrode 46b is provided so as to be located at the boundary between the side surface f2 facing to the proximal end and the top surface f1 or the bottom surface f3 of the multi-layer substrate 46A along the height direction. In the imaging device 40A, the end 48e of the shielded wire 48c may abut the shielded-wire connection electrode 46b, thereby to be positioned therein. In the imaging device 40A, the length r1 of the exposed internal insulating member 48b is longer than the length r2 from the end of the core connection electrode 46a to the side surface f2 facing to the proximal end. Preferably, the length r1 is substantially identical to the sum of the length r2 from the end of the core connection electrode 46a to the side surface f2 facing to the proximal end and a thickness r4 of the shielded-wire connection electrode 46b. With this, the end 48e of the shielded wire 48c may be in contact with and positioned to the shielded-wire connection electrode 46b. Furthermore, the shielded-wire connection electrode 46b and the end 48e of the shielded wire 48c may be in direct contact by abutting each other, whereby the connection between the shielded wire 48c and the shielded-wire connection electrode 46b may be further ensured.

Figure 6:
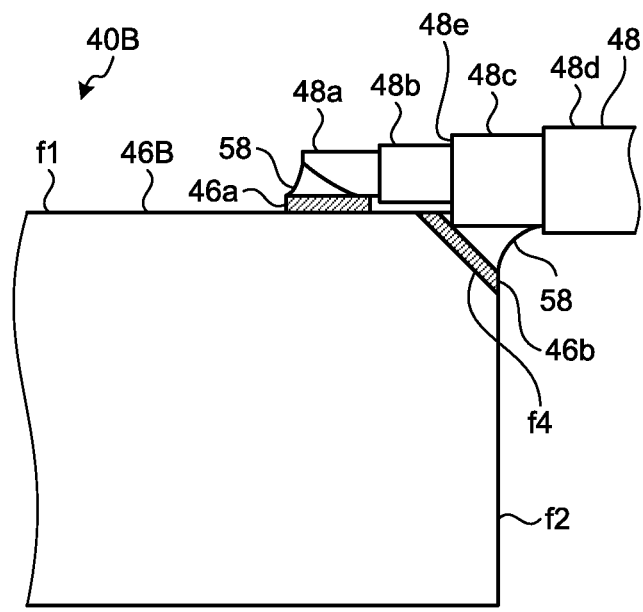
FIG. 6 is a partial side view of the proximal end part of a multi-layer substrate to which the signal cable is connected according to a modification 2 of the first embodiment of the present disclosure.

Furthermore, the shielded-wire connection electrode 46b may be formed on the surface that is adjacent to the surface extending along the height direction of the multi-layer substrate 46 and that faces to the proximal end. Additionally, the shielded-wire connection electrode 46b may be formed on a slope surface f4 provided between the top surface f1 and the side surface f2. FIG. 6 is a partial side view of the proximal end part of a multi-layer substrate 46B to which the signal cable 48 is connected according to a modification 2 of the first embodiment of the present disclosure.

In an imaging device 40B, the shielded-wire connection electrode 46b is formed on the slope surface f4 that is adjacent to the top surface f1 of the multi-layer substrate 46 and that faces to the proximal end. In the imaging device 40B, the end 48e of the shielded wire 48c may be in contact with and positioned to the shielded-wire connection electrode 46b. By forming the shielded-wire connection electrode 46b on the slope surface f4, the connection area of the shielded wire 48c and the shielded-wire connection electrode 46b may be increased, and the connection strength may be improved.

Second Embodiment

Figure 7:
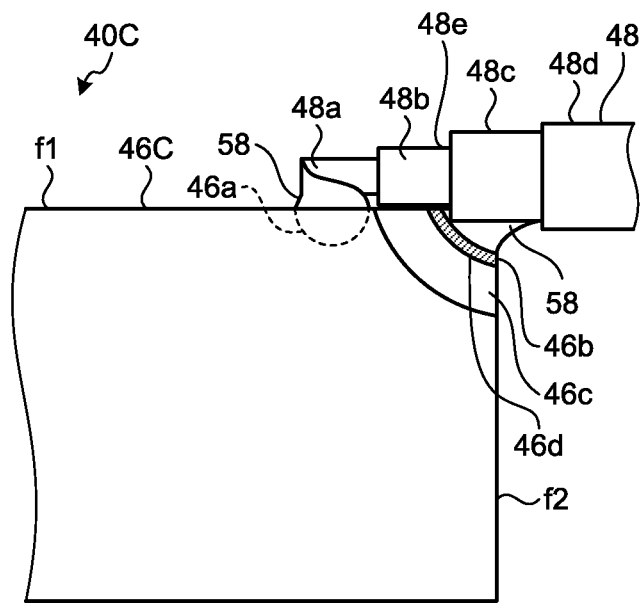
FIG. 7 is a partial side view of the proximal end part of a multi-layer substrate to which the signal cable is connected according to a second embodiment of the present disclosure.
Figure 8:
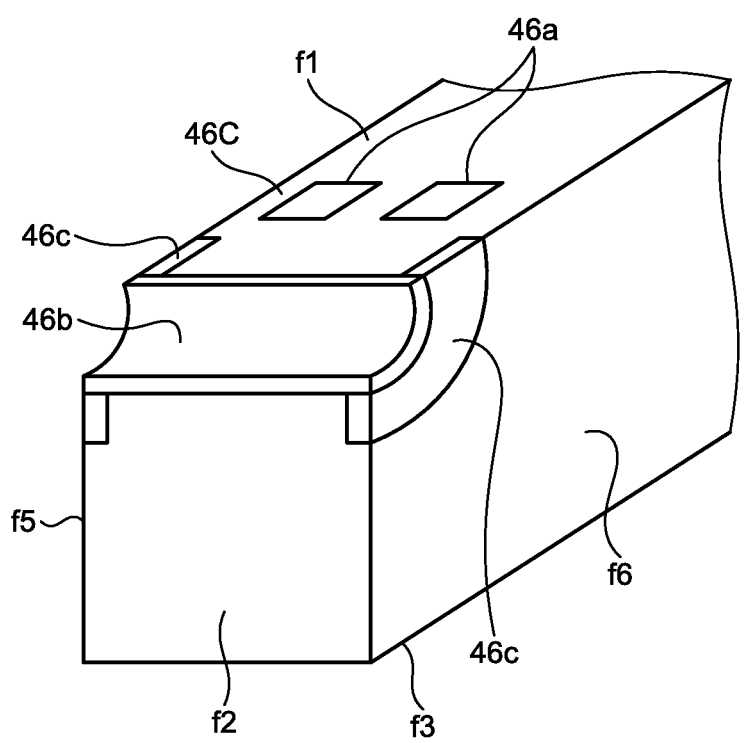
FIG. 8 is a partial perspective view of the proximal end part of the multi-layer substrate used according to the second embodiment.

FIG. 7 is a partial side view of the proximal end part of a multi-layer substrate to which the signal cable is connected according to a second embodiment of the present disclosure. FIG. 8 is a partial perspective view of the proximal end part of the multi-layer substrate used according to the second embodiment.

In an imaging device 40C according to the second embodiment, a notched and recessed corner portion 46d (FIG. 7) is provided between the top surface f1 of a multi-layer substrate 46C and the side surface f2 facing to the proximal end. The shielded-wire connection electrode 46b is provided on the corner portion 46d. Furthermore, conductive lands 46c are formed on side surfaces f5 and f6 adjacent to the corner portion 46d. With the imaging device 40C, the end 48e of the shielded wire 48c may be in contact with and aligned with the shielded-wire connection electrode 46b, and the length required to connect the core 48a and the shielded wire 48c on the multi-layer substrate 46C may be reduced. Furthermore, the core connection electrode 46a is embedded in the multi-layer substrate 46C, and its front surface is exposed on the surface f1.

The multi-layer substrate 46C used in the second embodiment is manufactured such that green sheets, each of which has a conductor layer and a via formed, are laminated and sintered to form an assembly of the multi-layer substrates 46C and then the assembly is divided into each piece. A tube-shaped conductive member having a flange area, which is to be the land, is embedded in the multi-layer substrate 46C for the end forming a through-hole and it is divided into each piece. With this, it is possible to manufacture the multi-layer substrate 46C including the shielded-wire connection electrode 46b on the corner section 46d and including the land that is adjacent to the corner section 46d. Similarly, an embedded electrode (VIA) is provided in the multi-layer substrate 46C and it is divided into each piece, whereby the core connection electrode 46a may be formed.

Figure 9:
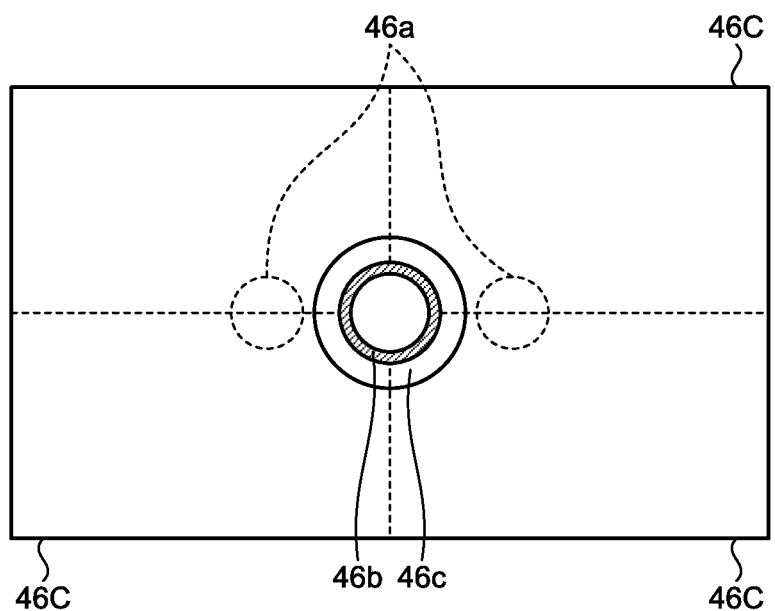
FIG. 9 is a diagram that illustrates a method for manufacturing the multi-layer substrate used in the second embodiment.

FIG. 9 is a diagram that illustrates a method of manufacturing the multi-layer substrate 46C used in the second embodiment. FIG. 9 is a diagram when the assembly is viewed from the side surface before the assembly is divided into the four multi-layer substrates 46C. As illustrated, the tube-shaped conductive member including the flange area is embedded in the center part of the four multi-layer substrates 46C. Furthermore, an embedded electrode is provided on the center line passing through the centers of the short sides of the assembly. The assembly is cut along the dotted line in FIG. 9, thereby to obtain four multi-layer substrates 46C, so that the flange area becomes the land 46c and the tube-shaped area becomes the shielded-wire connection electrode 46b. In the same manner, the embedded electrode becomes the core connection electrode 46a.

Figure 10:
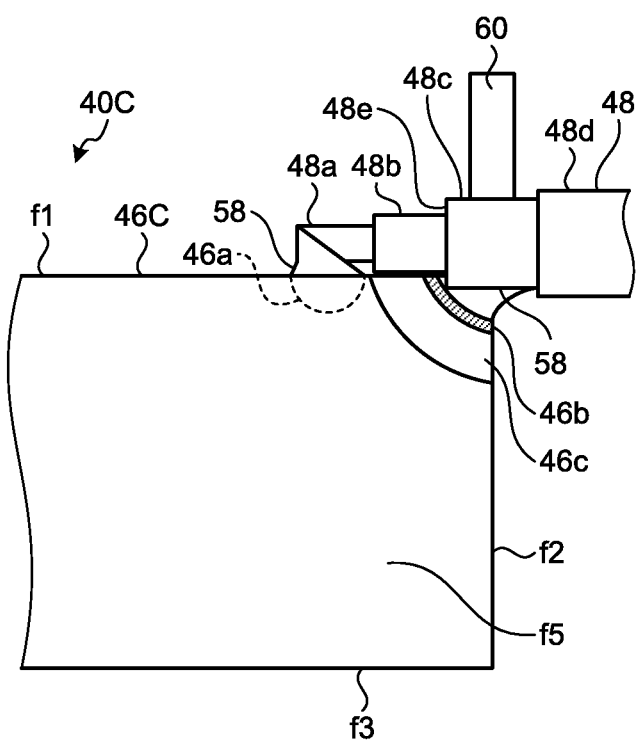
FIG. 10 is a diagram that illustrates the connection of the signal cable to the multi-layer substrate in the imaging device according to the second embodiment.

To connect the signal cable 48 to the multi-layer substrate 46C, after the shielded wire 48c is connected to the shielded-wire connection electrode 46b, the core 48a is connected to the core connection electrode 46a. To connect the shielded wire 48c, as illustrated in FIG. 10, it is preferable that a heater chip 60 applies heat to the shielded wire 48c in a contact or non-contact manner from the direction of the top surface f1 of the multi-layer substrate 46, and laser light or soft beam is emitted to apply heat from the direction of the side surface f5 or f6 to the conductive land 46c that is formed in the direction of the side surface f5 or f6 on the shielded-wire connection electrode 46b so that the solder 58 is melted and connected.

If the heater chip 60 applies heat to the shielded wire 48c from above, heat is transferred toward the proximal end side of the signal cable 48 and the solder 58 is sometimes melted insufficiently. However, the conductive land 46c is provided in the directions of the side surfaces f5 and f6 and the laser light or soft beam is emitted to the land 46c to apply heat so that the solder 58 may be melted in a short time and connection strength may be improved.

Furthermore, if the solder 58 is melted from the direction of the top surface of the shielded wire 48c and from the direction of the side surface f5 or f6 of the multi-layer substrate 46C, it is preferable that the amount of heat applied from the direction of the top surface is larger than the amount of heat applied from the direction of the side surface so that the temperature at the side of the top surface of the shielded wire 48c is higher. Thus, the melted solder 58 raises in the direction of the top surface of the shielded wire 48c, whereby a fillet may be easily formed and a connection area may be increased.

According to the present disclosure, signal cables may be easily connected to a multi-layer substrate, and the length of a hard part in an imaging device may be shortened.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
  at least one objective lens configured to collect light incident from an object to be imaged;
  an imaging sensor configured to receive light from the at least one objective lens and convert the received light to an electric signal;
  a multi-layer substrate electrically connected to the imaging sensor, the multi-layer substrate including electronic components installed thereon and electrically conductive layers and vias that are formed therein; and
  a collective cable including at least first and second coaxial cables electrically connected to the multi-layer substrate, wherein
  first and second core connection electrodes to which a first and second core wire of the first and second coaxial cables are respectively connected, the first core connection electrode being formed on a first surface of the multi-layer substrate and the second core connection electrode being formed on a second surface of the multilayer substrate, the first surface and the second surface each intersecting with a height direction of the multi-layer substrate, and
  first and second shielded-wire connection electrodes to which a first and second shielded wire of the first and second coaxial cables are respectively connected;
  wherein the first and second shielded-wire connection electrodes are formed on a side surface of the multi-layer substrate that is adjacent to both of the first and second surfaces of the multi-layer substrate, the side surface facing towards a proximal end and the collective cable extends towards the proximal end.

2. The imaging device according to claim 1, wherein:
  a first end of the first shielded-wire connection electrode is located at a first transition between the first surface and the side surface of the multi-layer substrate; and
  a second end of the second shielded-wire connection electrode is located at a second transition between the second surface and the side surface of the multi-layer substrate.

3. The imaging device according to claim 1, further comprising:
  a corner portion of recessed shape, the corner portion being located between the first surface and the side surface of the multi-layer substrate, wherein the first shielded-wire connection electrode is located on the corner portion; and
  a conductive land formed on a third surface of the multi-layer substrate adjacent to the corner portion.

4. An endoscope comprising:
  the imaging device according to claim 1; and
  an insertion unit configured to be inserted in a subject, the insertion unit comprising a distal end part having a cylindrical shape, the distal end part being formed of a material that is more rigid than a proximal portion of the insertion unit.

5. A method for manufacturing the imaging device according to claim 3, comprising:
  connecting the shielded wire of the coaxial cable to the shielded-wire connection electrode of the multi-layer substrate, the core of the coaxial cable, an internal insulating member that covers an outer circumference of the core, and the shielded wire that covers an outer circumference of the internal insulating member being gradually exposed from an external insulating member that covers an outer circumference of the shielded wire; and connecting the core to the core connection electrode, wherein the connecting of the shielded wire includes heating the shielded wire by using a heater chip from the height direction of the multi-layer substrate and applying heat by emitting laser light or soft beam to the conductive land formed in a direction of the third surface of the shielded-wire connection electrode from a direction of the third surface of the multi-layer substrate to melt solder so as to connect the shielded wire to the shielded-wire connection electrode.

6. The imaging device according to claim 1, wherein:

a first end of the first shielded-wire connection electrode is located offset from a first transition between the first surface and the side surface of the multi-layer substrate; and a second end of the second shielded-wire connection electrode is located offset from a second transition between the second surface and the side surface of the multi-layer substrate.

7. The imaging device according to claim 6, wherein:

the first shielded-wire connection electrode is offset from the first transition by a first distance that a first end face of the first shield wire protrudes onto the side surface when a first insulating member covering the first core wire is disposed to lay on the first surface; and the second shielded-wire connection electrode is offset from the second transition by a second distance that a second end face of the second shield wire protrudes onto the side surface when a second insulating member covering the second core wire is disposed to lay on the second surface.

* * * * *